(12) United States Patent
Slocum et al.

(10) Patent No.: US 7,025,324 B1
(45) Date of Patent: Apr. 11, 2006

(54) GATING APPARATUS AND METHOD OF MANUFACTURE

(75) Inventors: Alexander H. Slocum, Bow, NH (US); James R. White, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 209 days.

(21) Appl. No.: 10/336,625

(22) Filed: Jan. 3, 2003

Related U.S. Application Data

(60) Provisional application No. 60/345,024, filed on Jan. 4, 2002.

(51) Int. Cl.
 *F16K 31/00* (2006.01)
(52) U.S. Cl. .................. 251/11; 251/129.06; 251/231; 251/368
(58) Field of Classification Search ........... 251/129.06, 251/11, 231, 236, 248, 368
See application file for complete search history.

(56) References Cited

U.S. PATENT DOCUMENTS

| | | | |
|---|---|---|---|
| 4,581,624 A | 4/1986 | O'Connor | |
| 4,647,013 A | 3/1987 | Giachino et al. | |
| 4,756,508 A * | 7/1988 | Giachino et al. | 251/129.06 |
| 4,826,131 A | 5/1989 | Mikkor | |
| 5,029,805 A | 7/1991 | Albarda et al. | |
| 5,238,223 A * | 8/1993 | Mettner et al. | 251/368 |
| 5,325,880 A | 7/1994 | Johnson et al. | |
| 5,417,235 A * | 5/1995 | Wise et al. | 251/129.06 |
| 5,588,466 A | 12/1996 | Benz et al. | |
| 5,647,574 A | 7/1997 | Mettner et al. | |
| 5,681,024 A | 10/1997 | Lisec et al. | |
| 5,702,618 A | 12/1997 | Saaski et al. | |
| 5,705,070 A | 1/1998 | Saaski et al. | |
| 5,810,035 A | 9/1998 | Tekriwal et al. | |
| 5,839,467 A | 11/1998 | Saaski et al. | |
| 5,865,417 A * | 2/1999 | Harris et al. | 251/11 |
| 5,954,079 A * | 9/1999 | Barth et al. | 251/11 |
| 5,964,242 A | 10/1999 | Slocum | |
| 5,975,485 A | 11/1999 | Tsai et al. | |

(Continued)

*Primary Examiner*—John Bastianelli
(74) *Attorney, Agent, or Firm*—Daly, Crowley, Mofford & Durkee, LLP

(57) ABSTRACT

A gating apparatus for controlling the gap between two surfaces that includes an upper structure having a polished central region portion, an elastically deformable fulcrum structure, and an elastically deformable lever region. The upper structure can be fabricated from silicon using microelectromechanical system (MEMS) fabrication techniques. The gating apparatus also includes a lower structure coupled to the upper structure at the elastically deformable fulcrum structure. The upper structure, in response to a force, can bend about the fulcrum structure, thereby forming a variable gap between the polished central region portion and the lower structure. The variable gap can be used as a filter to filter fluids and mixed phase fluids. The structures can be made from a wide variety of materials including silicon, glass, ceramic, metal, and plastic.

39 Claims, 12 Drawing Sheets

U.S. PATENT DOCUMENTS

| | | |
|---|---|---|
| 5,984,257 A | 11/1999 | Baek et al. |
| 6,063,645 A | 5/2000 | Tasi et al. |
| 6,065,688 A | 5/2000 | Wilson et al. |
| 6,068,751 A | 5/2000 | Neukermans |
| 6,116,863 A | 9/2000 | Ahn et al. |
| 6,123,316 A | 9/2000 | Biegelsen et al. |
| 6,131,879 A * | 10/2000 | Kluge et al. ............ 251/129.06 |
| 6,142,444 A * | 11/2000 | Kluge .................... 251/129.06 |
| 6,168,395 B1 | 1/2001 | Quenzer et al. |
| 6,267,905 B1 * | 7/2001 | Silverbrook ............ 251/129.06 |
| 6,390,791 B1 * | 5/2002 | Maillefer et al. ....... 251/129.06 |
| 6,499,509 B1 * | 12/2002 | Berger et al. ........... 251/129.06 |
| 6,761,420 B1 * | 7/2004 | Maluf et al. ............ 251/129.06 |
| 6,914,785 B1 | 7/2005 | Slocum et al. |

\* cited by examiner

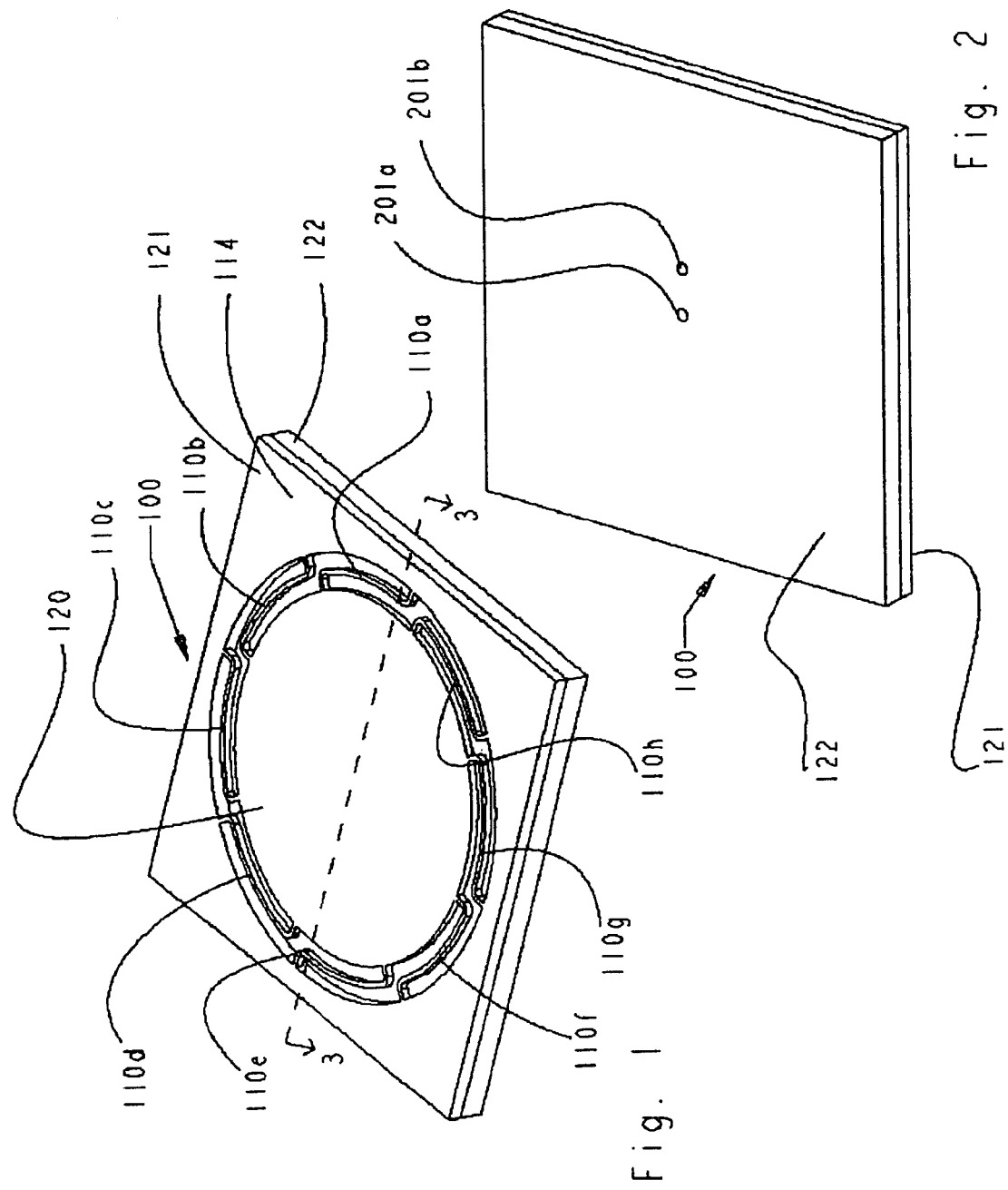

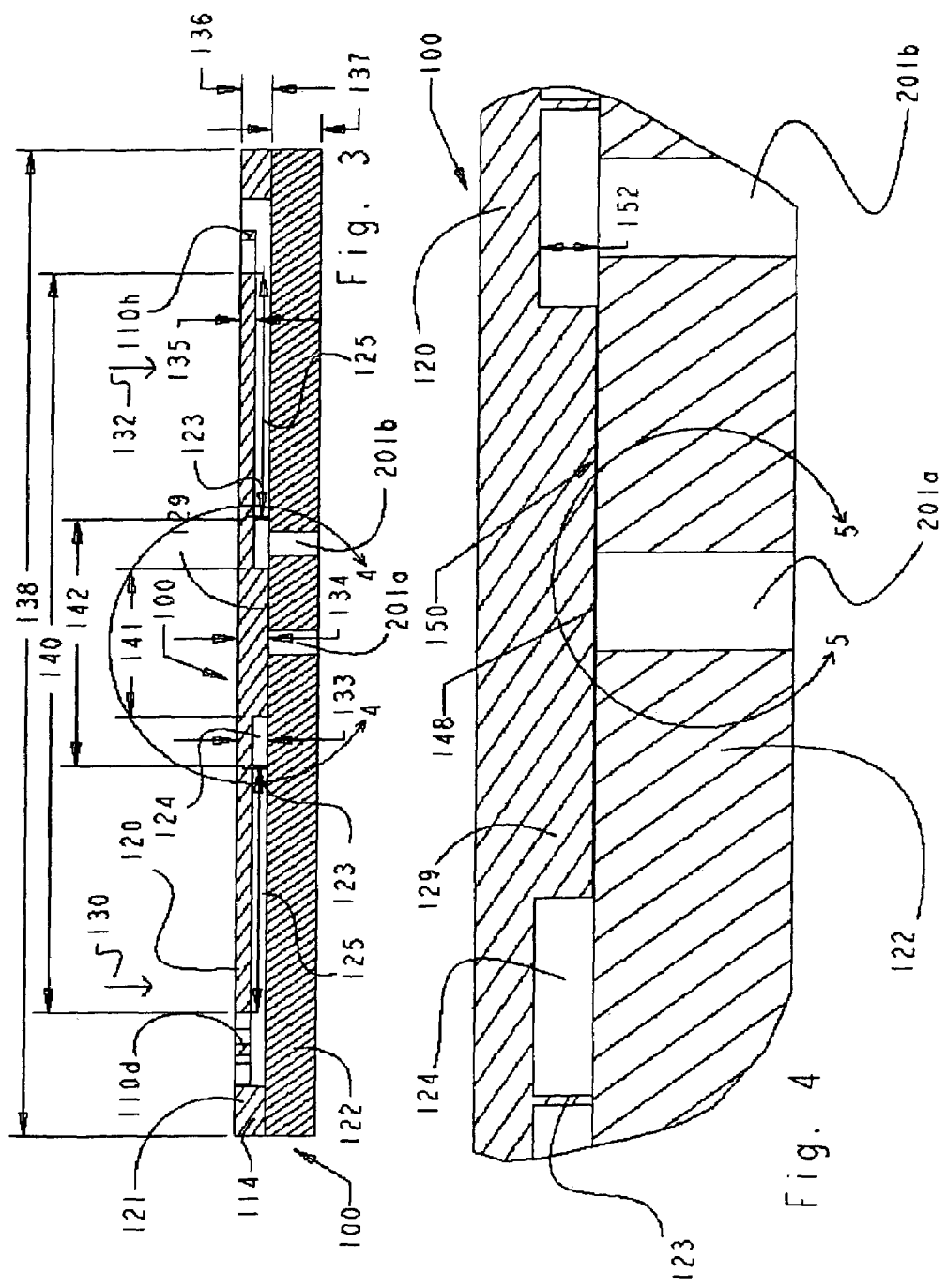

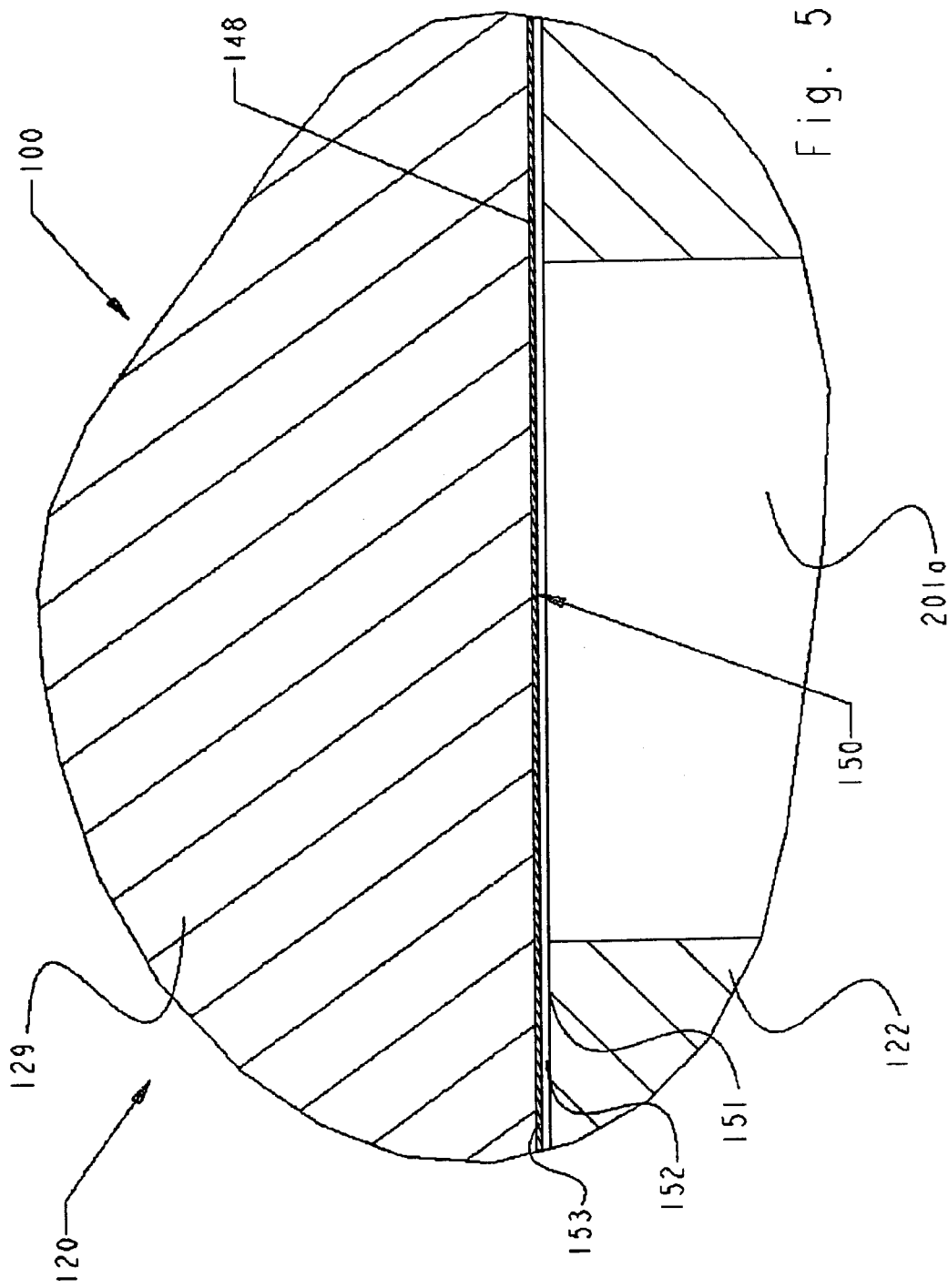

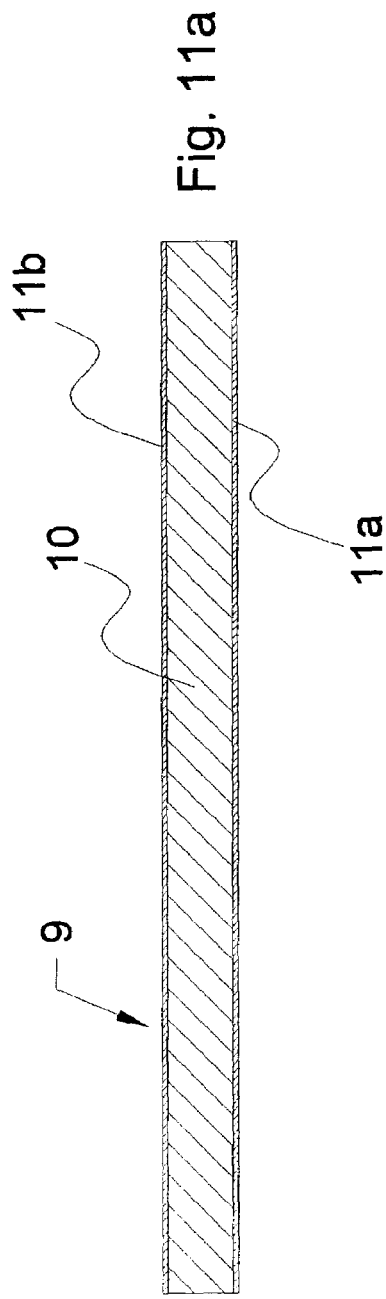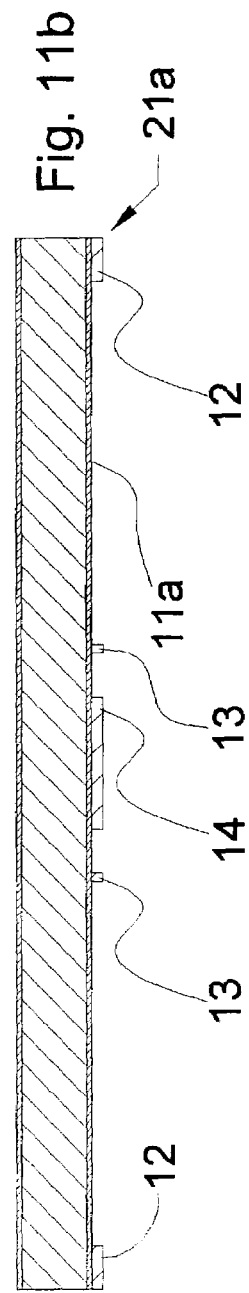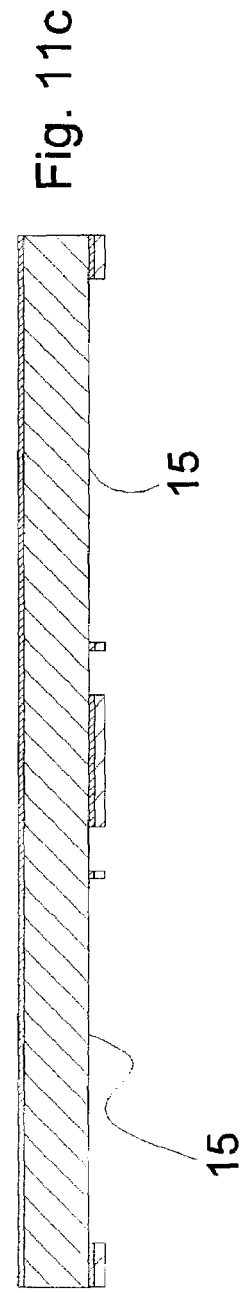

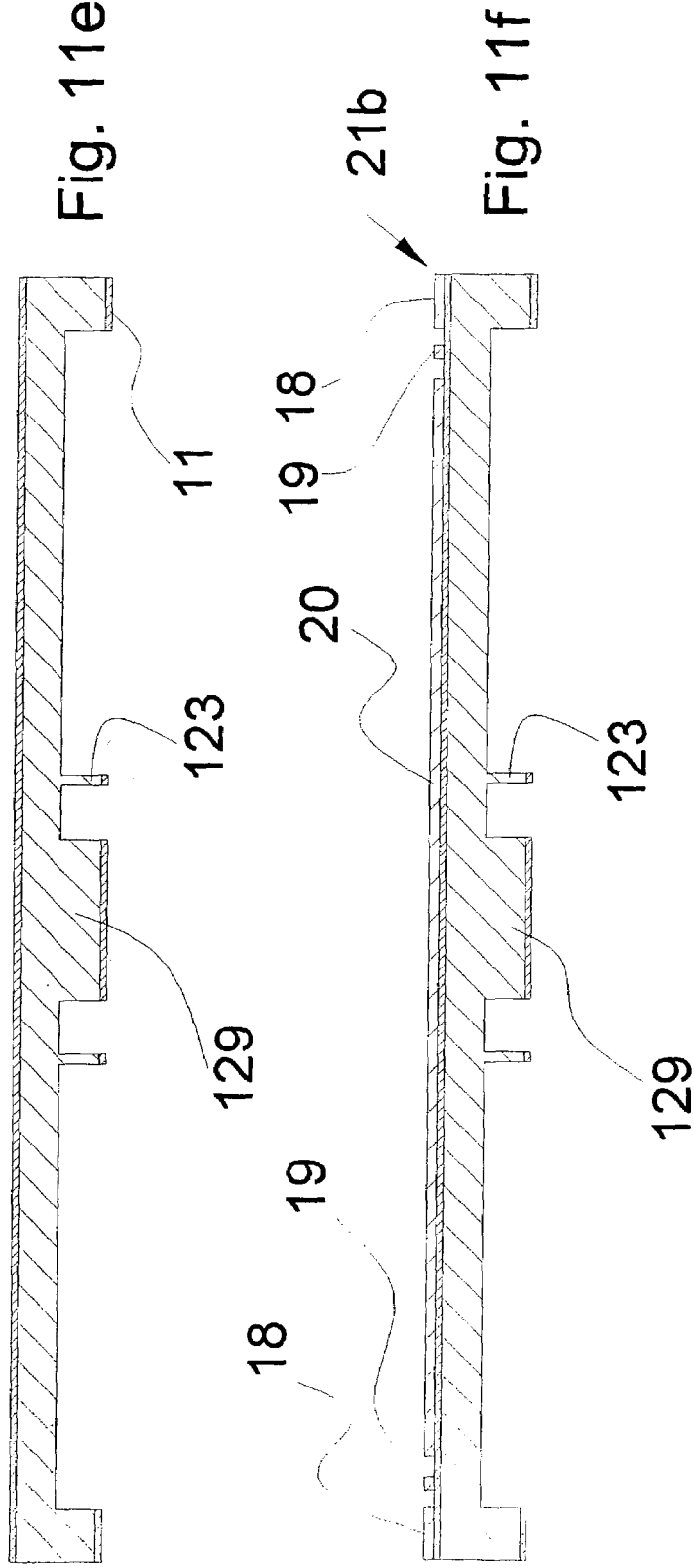

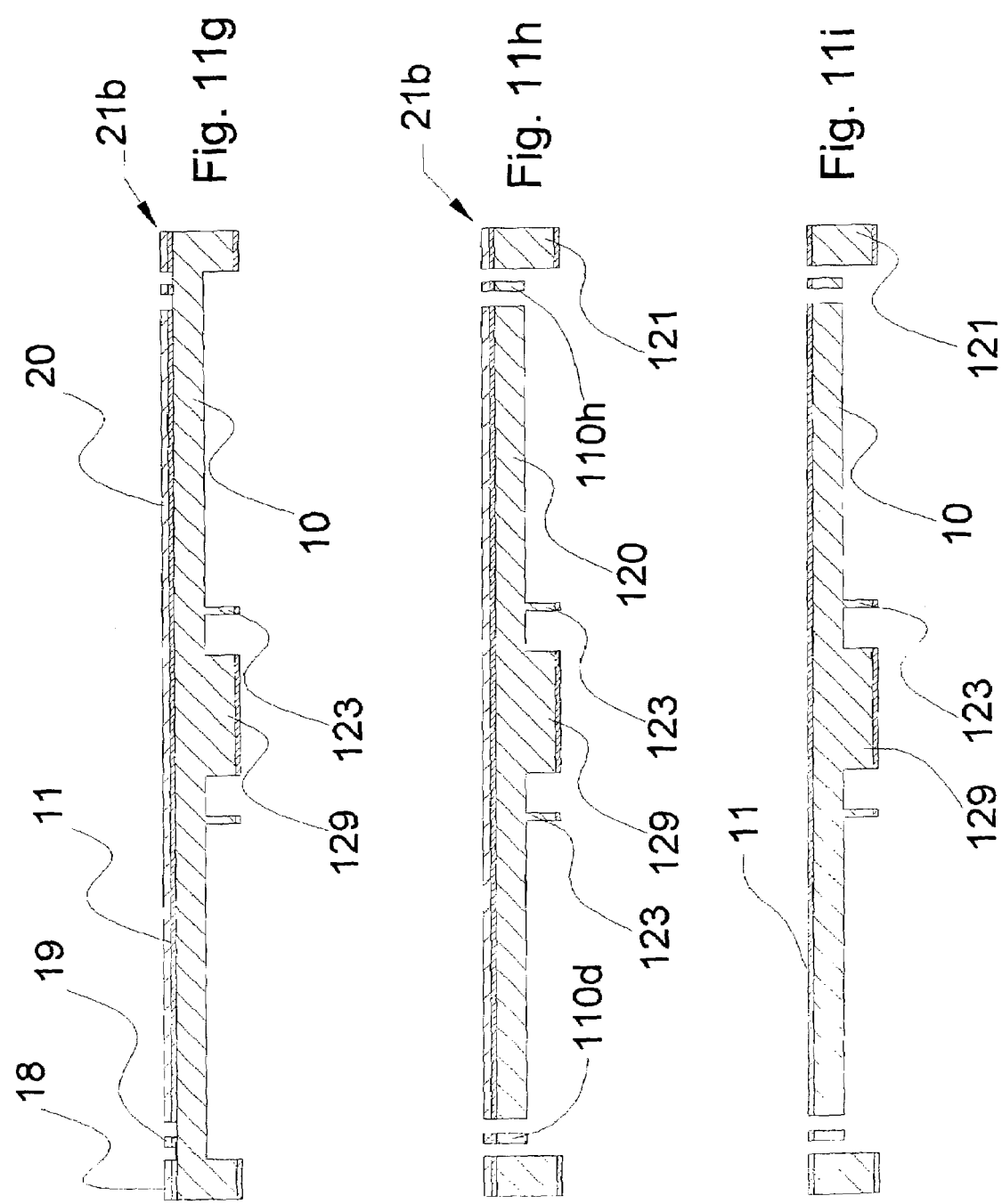

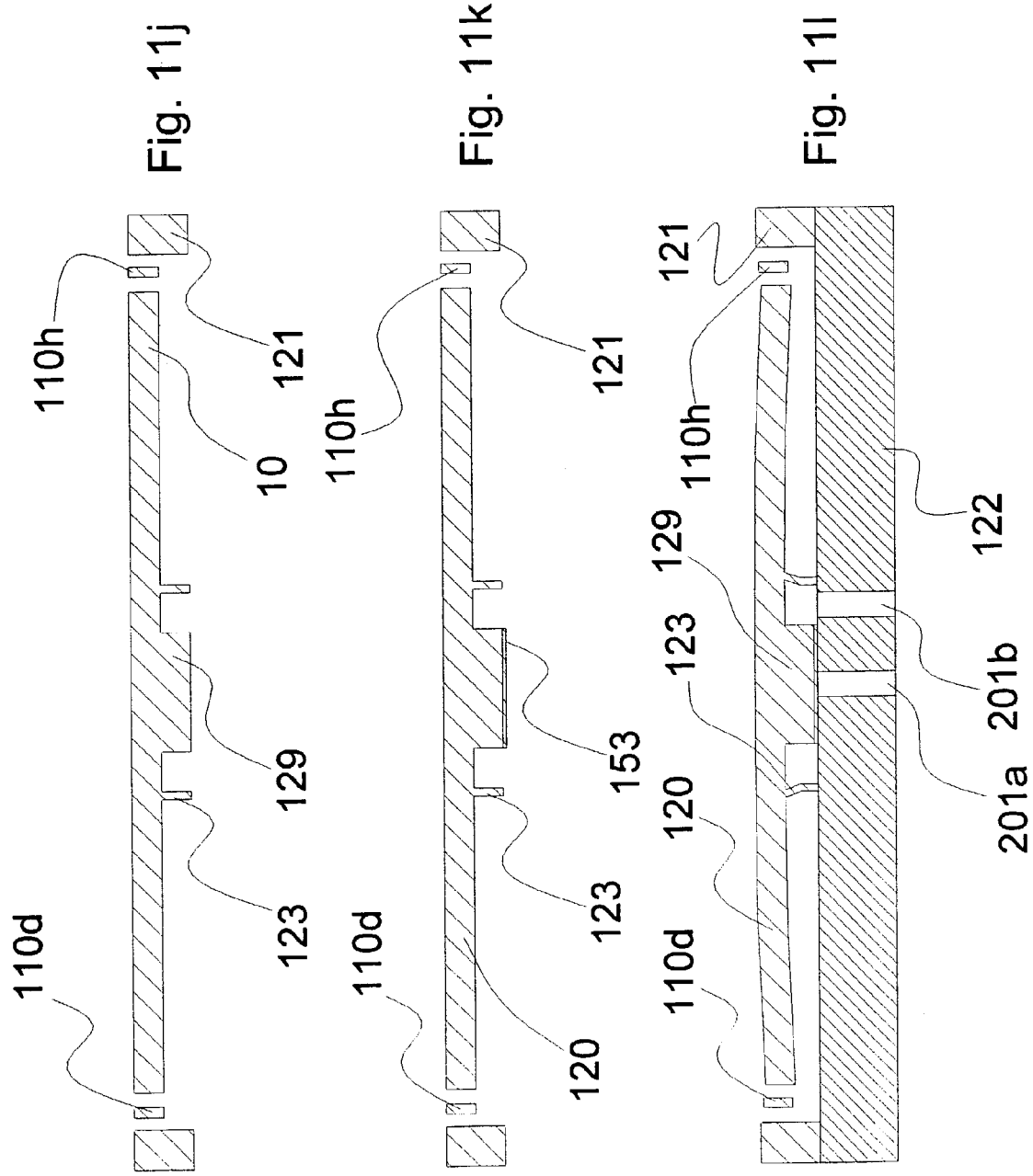

GATING APPARATUS AND METHOD OF MANUFACTURE

CROSS REFERENCE TO RELATED APPLICATIONS

This application claims the benefit of application No. 60/345,024 filed Jan. 4, 2002, which application is incorporated herein by reference in its entirety.

STATEMENT REGARDING FEDERALLY SPONSORED RESEARCH

This invention was made with government support under Contract No. 9900792 awarded by the National Science Foundation. The government has certain rights in this invention.

FIELD OF THE INVENTION

This invention relates generally to apparatus for controlling the flow of a fluid, where fluid is understood to mean either a liquid or a gas, and more particularly to an apparatus that can separate and/or sort solid particles suspended in the fluid.

BACKGROUND OF THE INVENTION

Biologists and chemists desire a technique for separating and/or sorting substances, molecule by molecule. For example, biologists and chemists would like to be able to determine which type of molecule(s) remains after a test reaction. In addition, biologists and chemists seek improved methods for processing molecules in a sample batch. It will be recognized that molecular dimensions are on the order of nanometers, thus, separating and/or sorting of molecules has been difficult to achieve. In addition, process controls require the use of proportional flow control valves.

In a conventional filtering process, a batch of material is presented to a filter having interleaved elements (e.g., many layers of extremely fine filter cloth). The unfiltered sample material passes through each of the filter layers so that a filtered sample material is provided at an output of the filter. With this filtering process, large amounts of the sample material are typically lost in the filter, since conventional filters enable only one molecule size to be sorted, and molecules with larger sizes are lost in the filter material. Thus, undesirably, filtering a batch of sample material using a conventional filtering process requires the use and loss of a large quantity of the sample material.

Biological samples, such as DNA, tend to be very expensive, on the order of tens of thousands of dollars per gram. Loss of sample material can be very expensive. Therefore, conventional filters have not provided an efficient mechanism for separating and/or sorting molecules of biological samples.

It would, therefore, be desirable to provide a mechanism with which particles, such as molecules, suspended in a fluid can be separated and/or sorted, while reducing the amount of sample material lost in the process. It would be further desirable to provide a mechanism with which the particles suspended in the fluid can be selectably separated and/or sorted, such that the same mechanism can be used to select and/or sort suspended particles having a variety of sizes. It would still furthermore be desirable to proportionally control the flow rate of a fluid to a very fine degree.

SUMMARY OF THE INVENTION

The basic structure and operation of the gating apparatus embodiments herein disclosed are novel improvements upon U.S. Pat. No. 5,964,242. The novel structures, designs and fabricating techniques of the present invention enable the commercial use of the present invention in a number of different applications particularly in microbiological fluid applications and the like. These novel features of the present invention include, among other features, the use of a structure which reduces practical sealing problems and provides a more uniform opening through which fluid can flow. In addition, the use of an elastically deformable fulcrum which is bonded to a lever structure provides an improved seal particularly for gases and very low viscosity fluids. In one embodiment the gating structure is provided having circular symmetry.

in accordance with the present invention a gating apparatus, includes an elastically deformable upper structure, having an elastically deformable lever region and a central region. The gating apparatus also includes a lower structure having a central region and an elastically deformable fulcrum structure disposed between and coupled to the upper and lower structures in proximity to the lever region. In operation, the upper structure bends about the elastic fulcrum structure in response to a force, therefore opening a gap between the central region of the upper structure and the central region of the lower structure. Changing the force changes the size of the gap, and thus the gating apparatus is provided with a controllable gap.

With this particular arrangement, the variable gap provides an opening that can operate as a filter to a mixed phase fluid, or as a proportional flow control valve for a fluid or gas. When the mixed phase fluid is introduced toward the variable gap, particles suspended in the mixed phase fluid that are larger than the variable gap cannot pass through the variable gap, while particles smaller than the variable gap can pass through the variable gap. Therefore, the gating apparatus provides a filter with which particles, such as molecules, suspended in a fluid can be separated and/or sorted. Substantially no material is lost in the filter. The gating apparatus, having the variable gap, also provides a filter with which the particles suspended in the fluid can be selectably separated and/or sorted. The same gating apparatus can be used to select and/or sort suspended particles having a variety of sizes, or control the flow of a fluid.

In one exemplary embodiment, the upper structure is provided having a shape which is substantially circularly symmetric (polygonic or circular) and is also provided having one surface which is essentially flat. Also, in some embodiments, the fulcrum structure is provided as part of the upper structure and is coupled to the lower structure. In a preferred embodiment, the fulcrum structure is coupled to the lower structure using a bonding technique. In other embodiments, however, the fulcrum structure is provided as part of the lower structure and is coupled to the upper structure. In a preferred embodiment, the fulcrum structure is coupled to the upper structure using a bonding technique.

In accordance with another aspect of the present invention, a method for making an apparatus for controlling the flow of fluids includes etching a surface of a wafer to provide an upper structure having an elastically deformable lever region, a central region, and an elastically deformable fulcrum structure in proximity to the lever region, all formed by etching or other such bulk processing means which would also include injection plastic molding, deposition, and replication. The method also includes processing the central region by polishing or depositing material on the central region to provide a polished central region portion.

With this particular arrangement, the gating apparatus can be fabricated with a silicon wafer process compatible with microelectromechanical system (MEMS) fabrication techniques.

BRIEF DESCRIPTION OF TUE DRAWINGS

The foregoing features of the invention, as well as the invention itself may be more fully understood from the following detailed description of the drawings, in which:

FIG. 1 is an isometric view of a top side of a gating apparatus in accordance with the present invention;

FIG. 2 is an isometric view of a bottom side of the gating apparatus of FIG. 1;

FIG. 3 is a cross sectional view of the gating apparatus taken across lines 3—3 of FIG. 1;

FIG. 4 is an enlarged cross sectional view of the gating apparatus taken across lines 4—4 of FIG. 3;

FIG. 5 is a still further enlarged cross sectional view of the gating apparatus taken across lines 5—5 of FIG. 4;

FIGS. 11a–11l are a series of cross-sectional views showing steps in the fabrication of a gating apparatus using microelectromechanical Systems (MEMS) manufacturing techniques.

DETAILED DESCRIPTION OF THE INVENTION

Figure 6:
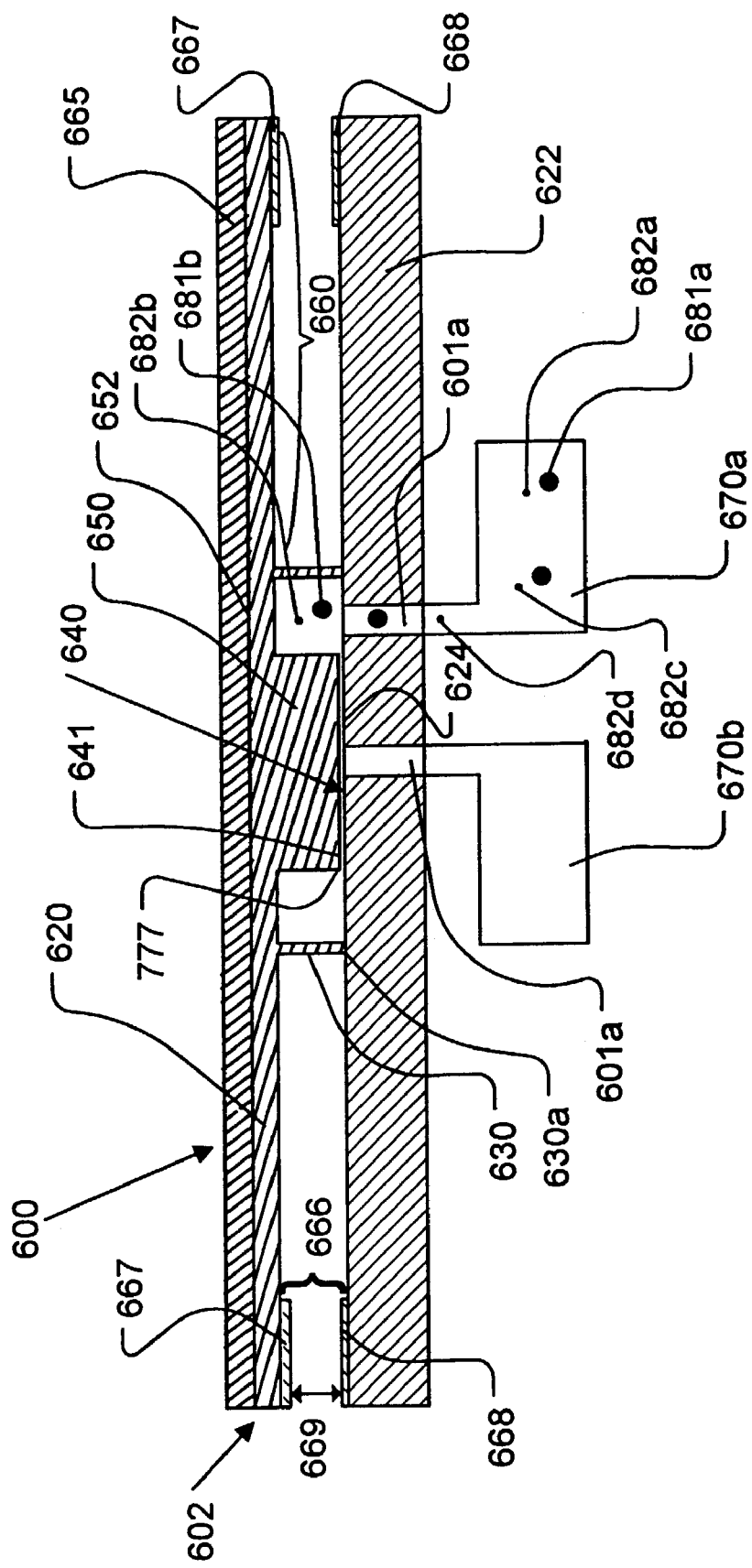
FIG. 6 is a pictorial cross sectional view of a gating apparatus shown in a closed state.

Before describing a gating apparatus and method of manufacture in accordance with the present invention, some introductory concepts and terminology are explained. As used herein, the term fluid is used to refer to either a liquid or a gas. The term mixed phase fluid refers herein to a substance comprised of a liquid and/or a gas with a solid suspended therein. Or a liquid/gas mixture or a mixture of immiscible liquids or gases. Also, it should be appreciated that the terms "upper", "lower", "right", "left", and so forth have been used herein merely for convenience to describe the present invention and its parts as oriented in the drawings. It is to be understood, however, that these terms are in no way limiting to the invention since such invention may obviously be disposed in different orientations when in use. It should also be understood that the general concepts of the present invention are illustrated herein with reference to structures having specific shapes. It should be understood that the specific shapes referenced herein are intended as illustrative and not intended as limiting and those of ordinary skill in the art will appreciate that other shapes may also be used.

Referring now to FIG. 1, the gating apparatus 100 includes an upper structure 121 and a lower structure 122, also referred to herein as an upper plate 121 and a lower plate 122. The upper structure 121 includes an inner portion 120 and an outer portion 114 coupled together with flexural beams 110a–110h. Together, the inner portion 120, the outer portion 114, and the beams 110a-110h form a flexure. In response to a force, the inner portion 120 can move perpendicular relative to the outer portion 114, and the beams 110a–110h bend accordingly.

The amount of movement depends upon the strength of the force. The upper structure 121 is bonded to the lower structure 122 with bonds described below. In a first bond, a surface of the outer portion 114 of the upper structure 121 is bonded to a surface of the lower structure 122. In a second bond, as described more fully below, a central region of the inner portion 120 is bonded to the lower structure 122 in a particular way that allows the inner portion 120 to bend in the plane of the inner portion 120 in response to particular forces.

Referring now to FIG. 2, in which like elements of FIG. 1 are shown having like reference designations, the gating apparatus 100 includes the lower structure 122 and the upper structure 121. The lower structure 122 has first and second fluid flow channels 201a, 201 respectively passing completely through the lower structure 122.

Referring now to FIG. 3, in which like elements of FIGS. 1 and 2 are shown having like reference designations, a cross section of the gating apparatus, taken along lines 3—3 shown in FIG. 1, shows the upper structure 121 including the inner portion 120 having an elastically deformable fulcrum structure 123 and a central region 129. Each of the fulcrum structure 123 and the central region 129 can have a substantially circular symmetric shape, where the fulcrum structure 123 has an annular (continuous or segmented) ring shape with a diameter greater than the diameter of the central region 129. While the central region 129 and the fulcrum structure 123 are shown having cylindrical shapes, in alternate embodiments, they can have any three dimensional polygonal shape. The fulcrum structure 123 is substantially stiff in compression and compliant in bending; and the latter can be enhanced by making the annular ring segmented, or even discrete such as a 3 point support, but then a larger dead volume will exist.

The inner portion 120 also includes a lever region 125 between the fulcrum structure and the beams 110a–110h. As will become apparent from discussion below, a force 130 applied to the lever region in a direction perpendicular to a surface of the lower structure 122 acts to bend the inner portion 120 of the upper structure 121 about the fulcrum structure 123. Similarly, a force 132 alone, or together with the force 130, generates a similar bending effect. The forces 130, 132 can be forces applied at points on the lever region 125, or they can comprise a distributed force, for example, a force equally applied about an annulus within the lever region 125.

The first fluid flow channel 201a is aligned with the central region 129 and the second fluid flow channel 201b is aligned with an annular chamber 124 between the fulcrum structure 123 and the central region 129.

The upper structure 121 has a thickness 136, the central region 120 has a thickness 134, the fulcrum structure has a thickness 133, and the lever region 125 has a thickness 135. The upper structure 121 has a diameter 138, the inner portion 120 has a diameter 140, the central region 129 has a diameter 141, and the fulcrum structure has a diameter 142. The lower structure has a thickness 136 and a diameter, which can be the diameter 138. In one particular embodiment, the upper structure 121, the central region 120, and the fulcrum structure 123 have respective thicknesses 136, 134, 133 that are substantially the same and equal to about 300 microns, the thickness 135 of the lever region 125 is about 150 microns, the thickness 137 of the lower structure 122 is about 500 microns, the diameter 140 of the inner portion 120 is about 8 mm, the diameter 141 of the central region 129 is about 1 mm, and the diameter 142 of the fulcrum structure 123 is about 2 mm. However, it should be appreciated that, in other embodiments, the inner portion 120, the central region 129, and the fulcrum structure 123 can have a wide range of diameters. Similarly, in other embodiments, the upper structure 121, the central region 129, the fulcrum structure 123, the lever region 125, and the lower structure 122 can have a wide variety of thicknesses. In all cases, the diameters and thicknesses are selected to give a desired mechanical impedance and flow resistance as will be known to those skilled in the art of the design of microfluidic systems.

Also, while eight beams 110a–110h are shown, in other embodiments, more than eight or fewer than eight beams can be used with this invention. Additionally, in still other embodiments, the inner portion 120 can be coupled to the outer portion 114 using structures other than the beams 110a–110h, for example with radial beams. In further embodiments, the inner portion 120 is coupled to the outer portion 114 using no beams, for example, with an elastic membrane, or by a temporary structure that is removed once the upper structure 121 is bonded to the lower structure 122.

The upper structure 121, including the inner portion 120, the outer portion 114 and the beams 110a–110h can be comprised of silicon, and the fabrication of the upper structure 121 can be done as a multi-step silicon etching process. However, in other embodiments, other materials, for example ceramic, glass, or a polymer, can be used.

The lower structure can be comprised of any rigid material, for example glass, silicon, ceramic, or some polymers. In one particular embodiment, the lower structure is comprised of Pyrex® glass. It will become apparent from discussion below that the upper structure 121 and the lower structure must be capable of having highly polished surfaces when the gating structure 100 is used to provide nanometer scale filtering or picoliter/second flow control. However, in other embodiments, the upper structure 121 and the lower structure 122 have moderately polished surfaces, or no polished surfaces depending on the application. For example, in macro versions of the gating apparatus, where the characteristic diameter may be on the order of many centimeters or even as large as a meter, as-machined or molded surfaces may be sufficient.

Referring now to FIG. 4, in which like elements of FIGS. 1, 2, and 3 are shown having like reference designations, a cross section of the gating apparatus, taken along lines 4—4 shown in FIG. 3, shows the central region 129 having a surface 148, also referred to herein as a polished central region 148. The polished central region portion 148 has flat and smooth characteristics described below. The gating apparatus 100 is shown to be closed, wherein the polished central region portion 148 is in contact with the lower structure 122, therefore isolating the first fluid flow channel 201a from the second fluid flow channel 201b. The lower structure has a polished lower structure surface portion 151, also having flat and smooth characteristics described below.

The annular chamber 124 is provided between the fulcrum structure 123 and the central region 129. The annular chamber 124 is aligned with the second fluid flow channel 201b.

Referring now to FIG. 5, in which like elements of FIGS. 1, 2, 3, and 4 are shown having like reference designations, a cross section of the nanogate apparatus taken along lines 5—5 shown in FIG. 4, shows the polished central region portion 148 aligned with the first fluid flow channel 201a. The polished central region portion 148 can be proximate to, or in contact with the polished lower structure surface portion 151 depending upon whether the nanogate apparatus 100 is open or a closed. Here shown, the nanogate apparatus 100 is open, therefore having a gap 152 between the polished central region portion 148 and the polished lower structure surface portion 151. The gap 152 can be a variable gap 152, such that the gap size is determined by the magnitude the force 130, 132 (FIG. 3) applied to the lever region 125 (FIG. 3) that inner portion 120 about the fulcrum structure 123 (FIG. 3).

Through the variable gap 152, the first fluid flow channel 201a is connected to the second fluid flow channel 201b (FIG. 4) so that fluid can flow between the channels 201a, 201b. Particles suspended in the fluid having a size larger than the variable gap 152 cannot flow between the channels 201a, 201b. Thus, the variable gap 152 acts as a filter, allowing the fluid and small particles to pass between the fluid flow channels 201a, 201b, while not allowing larger particles to pass. Because the central region 129 (FIG. 4) has a relatively large annulus, the gap 152 is less likely to clog with filtered particles.

It will be appreciated that the smallest effective variable gap 152 provided by the gating apparatus 100 is (FIG. 1) affected by the surface finish or surface polish of the polished central region portion 148 and the polished lower structure surface portion 151. In one particular embodiment, the polished central region portion 148 and the polished lower structure surface portion 151 each have a surface polish better than five nanometers. In another embodiment, the central region portion 148 and the polished lower structure surface portion 151 each have a surface polish better than five angstroms. However, in still other embodiments, other surface polishes, or no surface polish, are possible with this invention.

In order to achieve the surface polish on the polished central region portion 148, layers 150 are disposed upon the surface 153 of the polished central region portion 148. In one particular embodiment, the layers 150 are comprised of a layer of chrome ten nanometer thick with a layer of platinum about 100 to 200 nanometers thick. However, in other embodiments, no layers 150 are provided or other layer materials are provided. For example, in other embodiments, the layers 150 can be comprised of at least one of a metal layer, a ceramic layer, an organic layer, and an inorganic layer, depending on the surface properties required for controlling the flow of different molecules and/or fluids.

As described above, the various dimensions associated with the upper structure 121 and the lower structure 122 can be provided over a variety of ranges and the upper structure 121 and the lower structure 122 can be comprised of a variety of materials. Therefore, the invention, is not limited to filtering of nanometer size particles suspended in a mixed phase fluid. Rather, the gating apparatus invention can filter a variety of particle sizes, from angstrom size to millimeter size. In general, the degree of polish should be 3–5 times smaller than the particle size. For example, if particles of size 15 nanometers are to be filtered, the polish should be better than 5 nanometers average roughness. It should be appreciated, however, that in some applications, it may be desirable or even necessary to vary from this general range and those of ordinary skill should recognize that the above range is exemplary and should not be construed as limiting.

Referring now to FIG. 6, a gating apparatus 600 is similar to or the same as the gating apparatus structure 100 of FIGS.

3–5. An inner portion 620 of an upper structure 602 (outer portion and beams not shown) has a central region 650 and a fulcrum structure 630, each with characteristics similar to the inner portion 120, the central region 129, and the fulcrum structure 123 of FIGS. 1–5. The fulcrum structure 630 is substantially rigid in compression but compliant in bending. A lever region 660, upon which a force is applied as described below, corresponds to the lever region 125 of FIG. 3. An annular cavity 682b is formed between the central region 650 and the fulcrum structure 630. The central region 650 has a polished central region portion 641 having layers 640, and the lower structure 622 has a lower structure polished region portion 624 aligned therewith. The polished central region portion 641 corresponds to the polished central region portion 148 (FIGS. 4, 5), the layers 640 correspond to the layers 150 (FIG. 5), and the lower structure polished region portion 624 corresponds to the lower structure polished region portion 151 (FIG. 5).

The lower structure 622 has a first fluid flow channel 601a aligned with the polished central region portion 641 and a second fluid flow channel 601b aligned with the annular cavity 682b.

A variable gap 777, here shown to be nominally closed, forms a variable connection between the first fluid flow channel 601a and the second fluid flow channel 601b. FIG. 6 actually shows a very small gap to indicate that the gating apparatus could be fabricated with a small nominal gap, or alternatively to illustrate that surface roughness always leaves some path for molecules. As will be shown in FIG. 11, the gating apparatus can be manufactured to have the gap completely closed and preloaded.

A mixed phase fluid 670a has small particles 682a, 682b and large particles 681a, 681b suspended therein. Because the variable gap 777 is closed, neither the single phase fluid 670a, the small particles 682a, 682b, nor the large particles 681a, 681b can pass through the variable gap 777 from the second fluid flow channel 601b to the first fluid flow channel 601a. Alternatively, because the variable gap 777 can have some leakage, only the single phase fluid 670a can pass through the variable gap 777, resulting in the single phase fluid 670b in the first fluid flow channel 601a.

The gating apparatus 600 includes an actuator 665, also called a deflection mechanism 665 herein, comprised, for example, of a piezoelectric layer 665 disposed on a surface of the inner portion 620. One of ordinary skill in the art will appreciate that the when a voltage is applied to the piezoelectric layer 665, the piezoelectric layer 665 tends to expand, causing the inner portion 620 to bend accordingly. The bending force is equivalent to the forces 130, 132 of FIG. 3. The force tends to bend the inner portion 620 about the fulcrum structure 630, therefore opening the variable gap 777 in proportion to the amount of bending, and therefore in proportion to the voltage applied to the piezoelectric layer 665. While the piezoelectric layer 665 is shown, in other embodiments the bending force can be provided in other ways, for example, with an electrostatic or electromagnetic actuator.

The gating apparatus 600 can also includes a deflection sensor 666 comprised of a first electrostatic plate 667 and a second electrostatic plate 668. When a signal is applied to the first plate 667, a corresponding signal is generated on the second plate 668, the magnitude of which is proportional to a separation 669 between the plates 667, 668. Therefore, the first and second plates 667, 668 can be used to provide an indication of the separation of the first and the second plates 667, 668, and, therefore, an indication of the amount of bending of the inner portion 620, and, therefore, and indication of the size of the variable gap 777. The signals associated with the first and the second plates 667, 668 are coupled to sensor electronics (not shown) that can provide the signal to the first plate 667 and receive the signal from the second plate 668, or visa versa, and that can control the piezoelectric deflection mechanism 665, and, therefore, the size of the variable gap 777.

While the electrostatic deflection sensor 666 comprising the first and second plates 667, 668 is shown, one of ordinary skill in the art will recognize that other deflection sensors can be used. For example, in one alternate embodiment, an inductive deflection sensor is used, or the gap can be measured with a laser.

Figure 7:
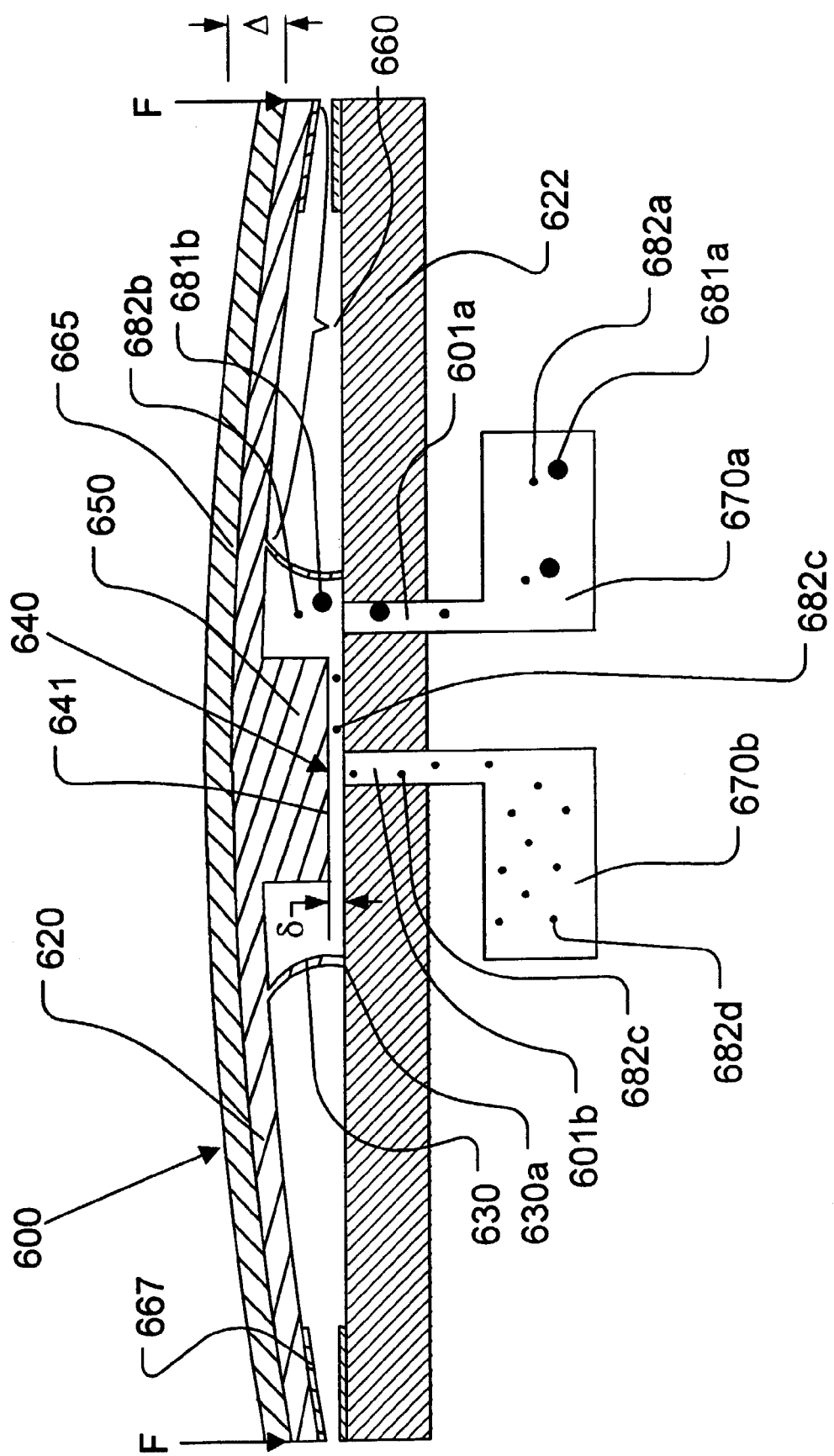
FIG. 7 is a pictorial cross sectional view of the gating apparatus of FIG. 6 shown in an open state.

Referring now to FIG. 7, in which like elements of FIG. 6 are shown having like reference designations, the variable gap 777 is open by an amount δ associated with bending of the inner portion 620 by a corresponding annular force F generated by the piezoelectric deflection mechanism 665 as described above. Edges of the inner portion 620 move by an amount Δ in response to the force F, thereby opening the variable gap by the amount δ. The ratio of Δ to δ corresponds to a mechanical advantage. In one particular embodiment, the mechanical advantage is ten to one.

However, in other embodiments, the mechanical advantage can be from two to one hundred to one. The mechanical advantage is related to the distance between the fulcrum structure 630 and the central region 650 compared with the length of the lever region 660.

It should be appreciated, however, that a wide range of other mechanical advantage ratios (i.e. ratios other than a ratio of 10:1) may also be used. The particular mechanical advantage ratio to use in any particular application will be selected in accordance with a variety of factors related to the particular gating apparatus structure used for the particular application as well as factors related to the particular application itself. Those of ordinary skill should recognize, therefore, that it may be desirable or even necessary to vary from the above general ranges and that the above ranges are exemplary and should not be construed as limiting.

Because the variable gap 777 is open an amount δ, small particles 682c, 682d can move from the second fluid flow channel 601b to the first fluid flow channel 601a. The gating apparatus 600, therefore, filters and sorts the small particles 682c, 682d.

Because the central region 650 is substantially thicker than the lever region 660, the central region 650 does not deform very much in bending when the inner portion 620 bends as shown. Therefore, the polished central region portion 641 remains substantially flat, and the variable gap 777 has substantially parallel surfaces when the inner portion 620 bends.

In addition to its use as a particle filter, substantially the same gating apparatus can be used as a flow control valve, where the region in the gap acts as a flow resistance, and thus the flow between the channels 601a and 601b will depend on the flow resistance in the gap and the pressure differential between the channels. Hence for example the gating apparatus can be used to control the flow of process fluids and gasses.

In one particular embodiment, the gating apparatus 100 can be constructed as a microelectromechanical system (MEMS). The uppers structure 620, including the fulcrum structure 630 and the central region having the polished central region portion 641 including the layers 640 can be fabricated with silicon etching and deposition procedures. In particular, the layers 640, as described above, can be deposited metal layers that can form a surface having a highly polished characteristic.

As described above, the inner portion 620 can be comprised of silicon and the lower structure 622 can be comprised of a glass such as Pyrex. With this particular arrangement, the inner portion 620 can be anodically bonded to the lower structure 622 at the joint 630*a*. In an alternate embodiment, the inner portion 620 is comprised of silicon the lower structure 622 is also comprised of silicon. With this alternate arrangement, the inner portion 620 can be fusion bonded to the lower structure 622 at the joint 630*a*. In this alternate arrangement, the lower structure, comprised of silicon, can have layers to provide a polished surface on the lower structure 622 in substantial alignment with the central region 650, the layers comparable to the layers 640.

It should be appreciated that in a preferred embodiment, the region 641 is provided as a relatively thin metal layer 641, such as a layer of chrome ten (10) nanometers thick with a platinum layer of about 100–200 nanometers on top of it. Such an approach allows the entire upper structure including the plate structure 620, the circular ring 630, and the center region 650 to be manufactured monolithically and have its bottom surface planer and polished. Then the metal layer 641 is applied while masking the bottom of the circular ring 630. Then the entire structure is selectively anodically bonded to the lower structure plate 622. The anodic bonding process, known to those skilled in the art of MEMS manufacture, causes the silicon surface of the bottom of the ring 630 to be attracted strongly to the top surface of the plate 622. The metal layer 641 prevents this attraction in its region, and thus the entire upper structure, due to the thickness of the metal layer, is actually preloaded against the bottom plate 622, which is important for sealing of the device.

It should also be appreciated that while the gating apparatus has been described having two fluid flow channels, for example the first and second fluid flow channels 601*a*, 601*b*, in alternate embodiments, only one of the first and the second fluid flow channel 601*b*, 601*a* is provided.

Figure 8:
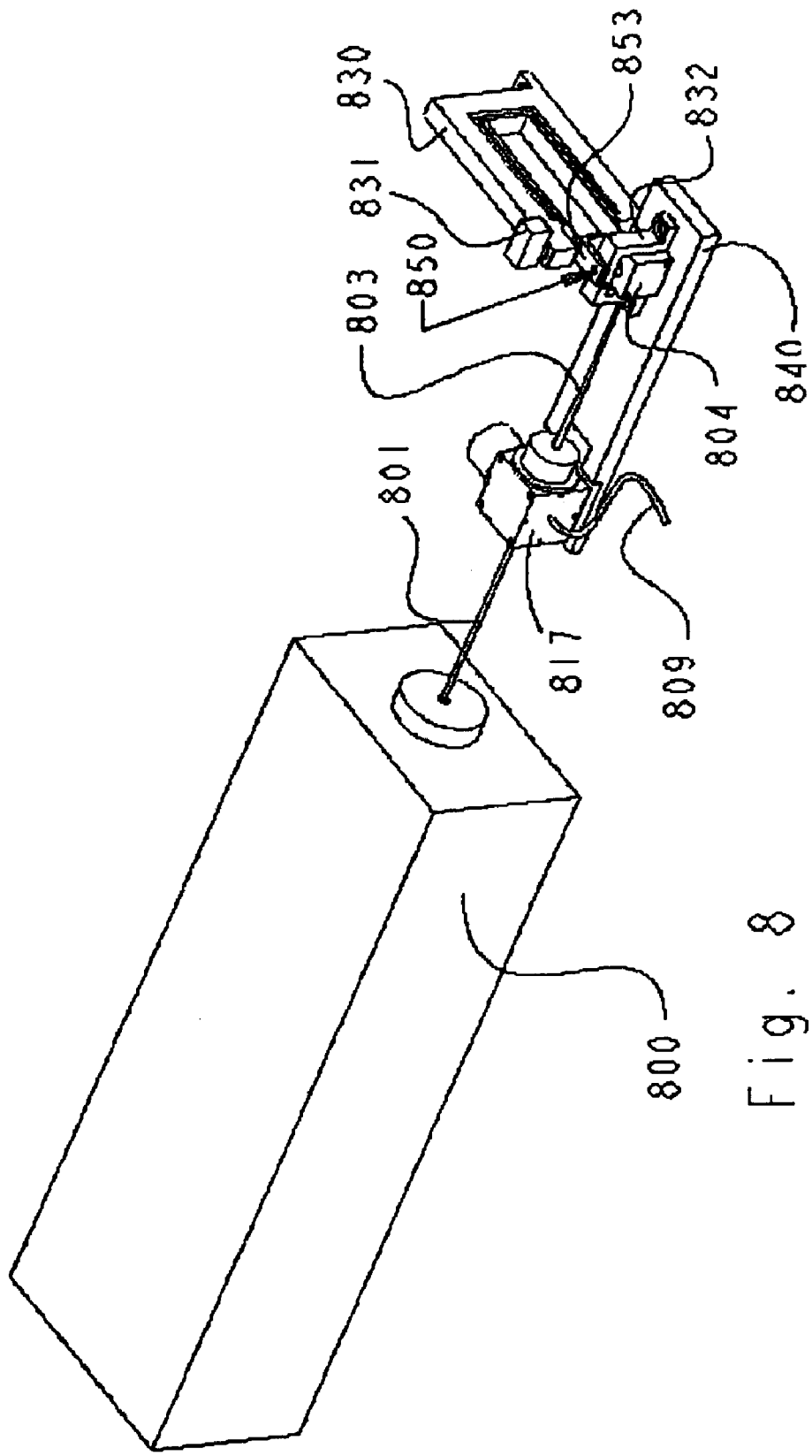
FIG. 8 is an isometric view of an exemplary system for directly measuring an opening of a gate plate of a gating apparatus using a laser interferometer.
Figure 9:
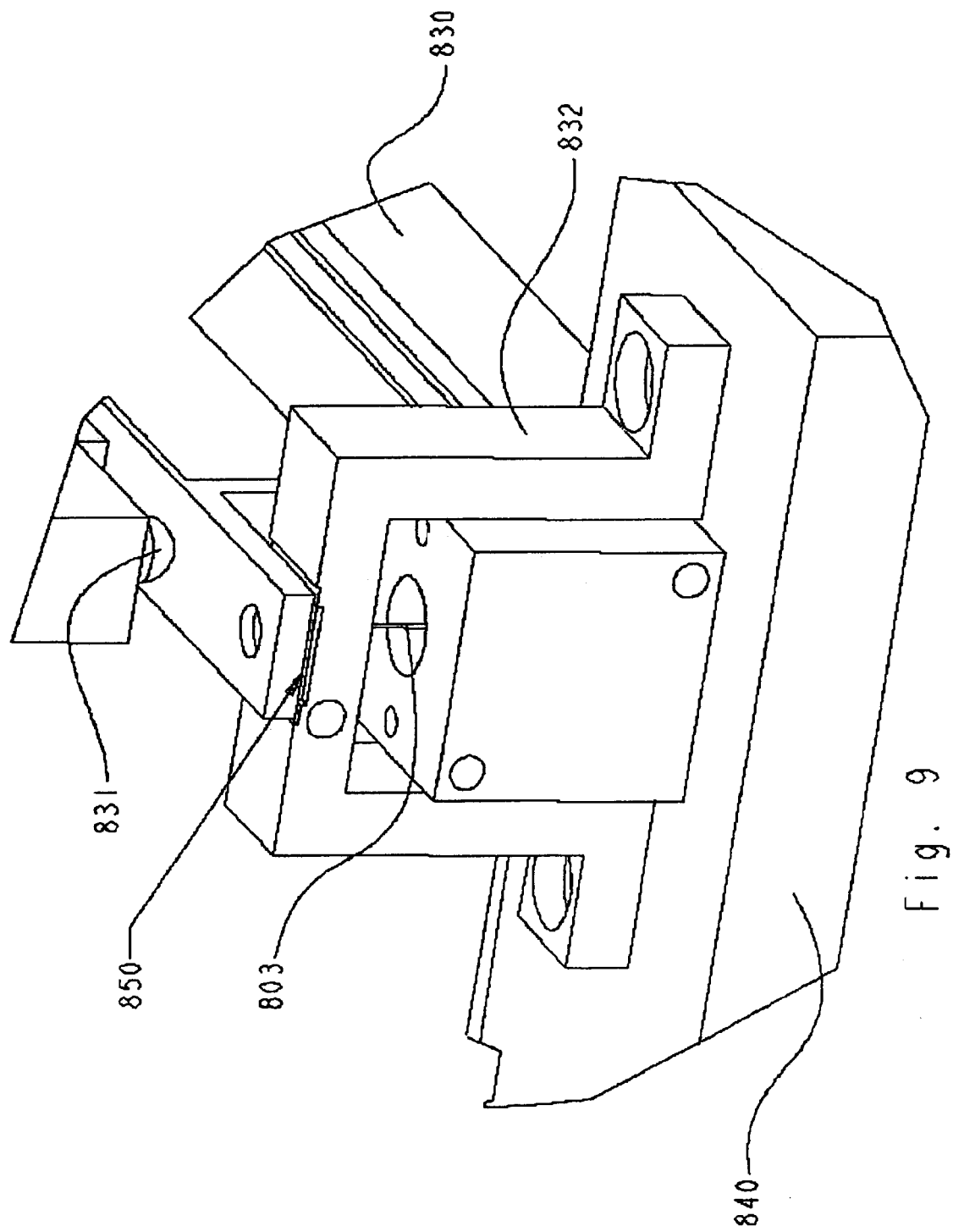
FIG. 9 is an enlarged isometric view of a portion of the system of FIG. 8.
Figure 10:
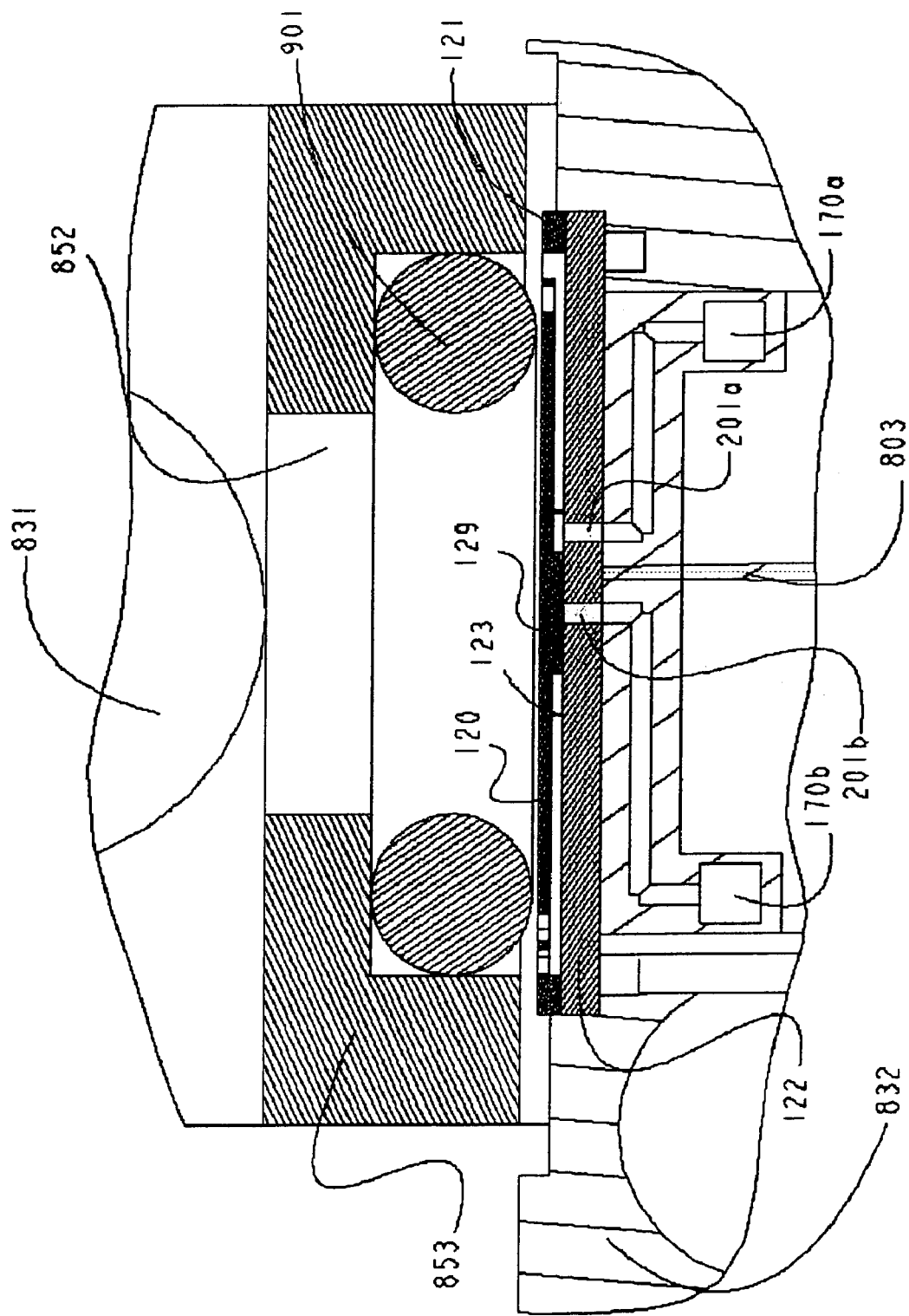
FIG. 10 is an enlarged partial section view of a portion of the system of FIG. 8.

Referring now to FIGS. 8–10 in which like elements are provided having reference designations throughout the several views, a system for directly measuring the width of an opening (e.g. gap 777 in FIG. 7) of a gate plate of a gating apparatus 850 includes a laser interferometer having a laser head 800 and a mounting structure 832 upon which the gating apparatus 850 is disposed. The laser interferometer may be of the heterodyne type sold by Zygo Corp.

The laser head 800 projects a beam of light 801 comprised of orthogonally polarized frequency shifted laser light. The light beam 801 passes through an interferometer with a lens 817, which reflects one of the beam components to an optical fiber 809 which carries the light to a signal processing board (not shown). The other beam passes through the interferometer and the lens focuses it to a point, but first it is bent by to a corner cube 804 which directs it to the back of the gating apparatus 850 which is mounted to a structure 832.

A flexure system 830 has a small motor/screw drive system 831, such as a Picomotor® made by Nu Focus Corp. Extension arm 853 transmits motion from the drive system 831 to the gating apparatus 850 via a flexure 830 and an O-ring 901 (FIG. 10), in a linear fashion devoid of rotation. The structure 840 maintains the required precision spacing between the optical elements and the structure 832 holding the gating apparatus. It should be appreciated that fluid lines are not shown here, because their use and mounting would be well known to anyone skilled in the art of precision fluid flow control.

Referring now specifically to FIG. 10 in which like elements of FIGS. 1–5, 8 and 9 are provided having like reference designations, an enlarged partial cross-section view through a typical experiment constructed using the gating apparatus is shown. It should be recognized that the interferometer beam 803 can pass through the clear lower plate structure 122 thereby impinging upon the top structure 120 (also referred to as the inner portion 120 of the upper structure 121). The lower plate structure is more fully described in association with FIG. 11*l*.

The Picomotor motor/screw drive system 831 exerts a force against portions of the flexure extension arm 853 which in turn exerts a force against the structure 120. The drive system 831 thus transmits deflection to the gating apparatus top structure 120 through the flexure extension arm 853 and the toroidal O-ring 901.

The gating apparatus base plate 122 is constrained against structure 832, which preserves the position and orientation of the gating apparatus relative to the interferometer beam 803. There is an opening 852 in the flexure extension arm 853 which allows direct access to the gating apparatus inner or central region 129, for example for the application of an external preload force, or for additional measurements of the shape of the diaphragm 120 during deflection. Chambers 170*a* and 170*b* contain fluids/particles and are connected to the fluid inlet and outlet ports 201*a* and 201*b*, respectively. Connections between chambers 170*a* and 170*b*, which are depicted schematically here, and apparatus for the injection or withdrawal of liquids or gases are not shown, but are well-known to those of ordinary skill in the art of precision fluid flow control.

The experimental set up shown in FIGS. 8, 9, and 10 uses a gating apparatus where external actuation and flow sources are used. As was depicted in FIGS. 6 and 7, a gating apparatus with an integral actuator, and capacitive or other displacement sensor, would be preferred in order to minimize system size and cost.

Steps in the fabrication process of a gating apparatus now will be described in conjunction with FIGS. 11*a*–11*l*. It should be noted that FIGS. 11*a*–11*l* are illustrative only, intended to aid in the understanding of the invention and an exemplary process for fabricating the invention.

FIGS. 11*a*–11*l* shows the manufacturing sequence for the gating apparatus, based on a nominally circularly symmetric design.

Referring now to FIG. 11*a*, a substrate 9 is shown having first and second oxidized surfaces 11*a*, 11*b*. In one embodiment, the substrate 9 may be provided as a section of a<100> double side polished (DSP) 300 micron thick silicon wafer 9 (the die) having a silicon core 10 and a 0.5 microns oxidized surface 11*a*, 11*b*.

Referring now to FIG. 11*b*, a photo resist layer 21*a* is deposited or otherwise disposed over selected portions 12–14 of surface 11*a*. As will be seen and described in conjunction with the FIGS. 11*c*–11*l* below, region 12 will define the outer structure (e.g. structure 114 in FIG. 3), region 13 will define the circular ring structure 123 (FIGS. 3, 4) and region 14 that will define the center gate structure 129 (FIGS. 3–5).

Referring now to FIG. 11*c*, the layer 11*a* is etched to expose a surface 15 of the silicon core 10. That is, regions of layer 11*b* not covered by the photo resist 21*a* are etched away. Thus the photo resist layer 21*a* acts as a mask during the etching of layer 11*b* to provide the regions 12–14 and to expose the silicon surface 15. As is known, the photo resist mask may be deposited in any pattern desired to provided structures of a desired size, shape and location.

Referring now to FIG. 11d, the silicon core 10 is further etched to expose a surface 16. In one particular embodiment, the surface 16 is provided by etching 150 microns deep using deep reactive ion etching (DRIE). As in conjunction with FIG. 11c, the photo resist layer 21a again acts as a mask during the etching of surface 15 layer.

Referring now to FIG. 11e, the wafer with the photo resist layer 21a removed is shown.

Referring now to FIG. 11f, a photo resist layer 21b is deposited or otherwise disposed over layer 11b. The photo resist layer 21b is patterned on the backside of substrate 9 to mask regions 18 for the outer structure, 19 to form the flexural supports, and 20 to form the plate structure.

Referring now to FIG. 11g, the layer 11b is etched to expose surfaces of the silicon core 10.

That is, regions of layer 11b not covered by the photo resist layer 21b are etched away. Thus the photo resist layer 21b acts as a mask during the etching of layer 11b to provide the regions 18–20 and to expose the silicon surface. As is known, the photo resist mask may be deposited in any pattern desired to provided structures of a desired size, shape and location.

Referring now to FIG. 11h, shows the wafer with the silicon 10 deep reactive ion etched to form the outer structure 121, the flexural supports 110d and 110h, for example, and the gate plate 120 with its circular ring support 123 and its center region 129.

FIG. 11i shows the wafer with the oxide resist 21b removed, and FIG. 11j shows the wafer with the oxide layers 11a, 11b removed.

Referring now to FIG. 11k, a metal layer 153 is disposed over a surface of region 129. The metal layer 153 can be provided using any technique well know to those of ordinary skill in the art. For example, metal layer 153 can be provided by depositing a composite conductive layer and patterning such a layer using well-known techniques. It should be appreciated that in a preferred embodiment, the metal layer 153 is provided as a relatively thin metal layer 153, such as a layer of chrome ten (10) nanometers thick with a platinum layer of about 100–200 nanometers on top of it. Such an approach allows the metal layer 153 to be provided as a planar, polished surface while allowing the entire upper structure to be manufactured monolithically. Then the metal layer 153 is applied while masking the bottom of the structures 123 (which define ring 630 in FIG. 6).

Referring now to FIG. 11l, the wafer (i.e. the wafer 10 in FIG. 11a after processing per the steps described in FIGS. 11a–11k) is anodically bonded to a bottom wafer 122 which is provided from a heat-resistant and chemical-resistant glass. The anodic bonding process, known to those of ordinary skill in the art of MEMS machines manufacture, causes the silicon surface of the bottom of the ring 123 to be attracted strongly to the top surface of the glass 122. The metal layer 153 prevents this attraction in its region, and thus the entire upper structure, due to the thickness of the metal layer, is actually preloaded against the bottom plate 122, which is important for sealing of the gate structure.

In general, it is desirable for the thermal expansion coefficient of the wafer 122 to be relatively close to that of the silicon wafer 10. Wafer 122 may be provided from any material which falls in the class of materials generally referred to as Pyrex®. In addition to the wafer 122 having a thermal expansion coefficient which is relatively close to that of the wafer 10, it is also desirable that the wafer 122 be of a material which allows wafer 10 to be securely attached thereto. Such attachment can be made suing a variety of techniques including boding techniques. In some embodiments, it is also desirable that the wafer 122 be provided from a material through which light can pass (e.g. an optically transparent material).

In one particular application, a specific type of Pyrex®, made by Corning—i.e. Pyrex® 7740 is preferred since the thermal expansion coefficient closely matches that of silicon. Also, it is relatively easy to make an anodic bond between the wafer 10 and the Pyrex® wafer 122. Furthermore, the clear Pyrex® makes it easy for optical measuring methods to be used to directly measure the opening of the gap between the plates (e.g. as described above in conjunction with FIGS. 8–10).

It should be appreciated that in some applications it may be desirable to provide layer 122 from a semiconductor material rather than from glass. In this case, a fusion bonding technique or other appropriately selected technique may be used to join the wafer 10 to the wafer 122.

It should also be appreciated that in some applications it may be desirable to provide the gating structure from ceramic, glass, metal, and plastic. In particular, in addition to semiconductor materials and Pyrex® as mentioned above, the upper structure, lower structure and fulcrum structure may all be provided from materials including but not limited to ceramic, glass, metal or plastic. Combinations of each of the above-mentioned materials may also be used. The particular material (or combination of materials) to use in any particular gating apparatus may be selected in accordance with a variety of factors associated with the particular application including but not limited to the desired filter characteristic provided by the gating apparatus (i.e. the size of the smallest particle which can be filtered), the type of material/fluid being filtered by the gating apparatus and cost. For example, in some applications which require a relatively low-cost gating apparatus, it may be desirable to provide a gating apparatus from molded plastic while still achieving acceptable filter performance characteristics.

As a further illustration of the usefulness and diversity of the structures and techniques of the invention, such shows promise for micro scale analytical instruments. In particular, the Pyrex bottom structure allows particles to be fluorescently tagged and then counted and observed using an optical fluorescence microscope that looks through the Pyrex.

The gating and controlling mechanisms of the invention have the potential to be to the chemical and biological communities somewhat of a tool that the transistor has been to the electronics community. It is therefore anticipated that further modifications of the invention will also readily occur to persons skilled in the art, and all such are deemed to fall within the spirit and scope of the invention as defined by the appended claims.

All references cited herein are hereby incorporated herein by reference in their entirety.

Having described preferred embodiments of the invention, it will now become apparent to one of ordinary skill in the art that other embodiments incorporating their concepts may be used. It is felt therefore that these embodiments should not be limited to disclosed embodiments, but rather should be limited only by the spirit and scope of the appended claims.

What is claimed is:

1. An apparatus for controlling the flow of gases, fluids and mixed phase fluids, the apparatus comprising:

an upper structure having an elastically deformable lever region and a polished central region; and a lower structure having a polished surface facing the upper structure;

a fulcrum structure disposed between the upper structure and the lower structure such that the fulcrum structure acts as a fulcrum about which the upper structure can be elastically deformed, to cause said upper structure central region to separate from the lower structure surface; and a deflection mechanism, wherein the deflection mechanism provides a deflection force upon the upper structure proximate the lever region and in a direction essentially perpendicular to the upper structure so as to bend the upper structure about the fulcrum structure.

2. The apparatus of claim 1, wherein the upper and lower structures are circularly symmetric shapes.

3. The apparatus of claim 1, wherein the fulcrum structure is provided as part of the upper structure and is bonded to the lower structure.

4. The apparatus of claim 1, wherein the upper structure is made from silicon.

5. The apparatus of claim 1, wherein the lever region is segmented to provide a pre-determined mechanical impedance.

6. The apparatus of claim 1, wherein the upper structure has a round shape.

7. The apparatus of claim 1, wherein the upper structure has a polygonal shape.

8. The apparatus of claim 1, wherein the central region has a round shape.

9. The apparatus of claim 1, wherein the central region has a polygonal shape.

10. The apparatus of claim 1, wherein the fulcrum structure has a round shape.

11. The apparatus of claim 1, wherein the fulcrum structure is provided as an elastically deformable fulcrum structure so as to form a flexural pivot.

12. The apparatus of claim 1, wherein the fulcrum structure is provided as a rigid structure and the apparatus further includes a mechanical pivot disposed at an interface between the fulcrum and the upper structure.

13. The apparatus of claim 1, wherein the fulcrum structure has a polygonal shape.

14. The apparatus of claim 1, wherein the fulcrum structure is segmented.

15. The apparatus of claim 1 wherein the fulcrum structure has a linear beam shape.

16. The apparatus of claim 1 wherein the fulcrum structure has a discrete number of points of support.

17. The apparatus of claim 1, wherein the lower structure has a round shape.

18. The apparatus of claim 1, wherein the lower structure has a polygonal shape.

19. The apparatus of claim 1, wherein the polished central region comprises a layer deposited on the central region.

20. The apparatus of claim 19, wherein the deposited layer has a surface finish better man five angstroms.

21. The apparatus of claim 19, wherein the deposited layer has a surface finish better than five nanometers.

22. The apparatus of claim 19, wherein the deposited layer comprises at least one of a metal layer, a ceramic layer, an organic layer, and an inorganic layer.

23. The apparatus of claim 1, wherein a seated cavity structure is bounded by the central region, the lever region, the fulcrum structure, and the lower structure.

24. The apparatus of claim 1, wherein the lower structure is comprised of glass or ceramic.

25. The apparatus of claim 1, further comprising an anodic bond between the fulcrum structure and the lower structure.

26. The apparatus of claim 1, wherein the lower structure is comprised of silicon.

27. The apparatus of claim 26, wherein the coupling between the fulcrum structure and the lower structure is provided by a fusion bond between the fulcrum structure and the lower structure.

28. The apparatus of claim 1, wherein the lower structure polished surface is disposed toward the polished central region of the upper structure; the fulcrum structure and the polished central region are disposed toward the lower structure polished surface, and the polished central region of the upper structure and the lower structure polished surface have a variable gap therebetween.

29. The apparatus of claim 28, wherein the polished lower structure surface has a surface finish better than five angstroms.

30. The apparatus of claim 28, wherein the polished lower structure surface has a surface finish better than five nanometers.

31. The apparatus of claim 28, further comprising:
a first fluid flow channel through the lower structure, wherein the first fluid flow channel is disposed into the variable gap.

32. The apparatus of claim 31, further comprising:
a second fluid flow channel through the lower structure, wherein the second fluid flow channel is disposed into a sealed cavity structure, the sealed cavity structure bounded by the central region, the lever region, the fulcrum structure, and the lower structure polished surface, and wherein the variable gap connects the first and second fluid flow channels.

33. The apparatus of claim 1, wherein the lever region in combination with the fulcrum structure provide a mechanical advantage to the deflection mechanism of between two to one and one hundred to one.

34. The apparatus of claim 1, wherein the deflection mechanism is a piezoelectric actuator mechanism.

35. The apparatus of claim 1, wherein the deflection mechanism is a thermoelectric expansion actuator mechanism.

36. The apparatus of claim 1, wherein the deflection mechanism is a electrostatic actuator mechanism.

37. The apparatus of claim 1, further comprising:
a deflection sensor coupled to at least one of the upper structure and the lower structure, provided to sense the position of the upper structure relative to the lower structure.

38. The apparatus of claim 37, wherein the deflection sensor comprises:
a first capacitive plate disposed upon the upper structure surface and directly opposing a second capacitive plate disposed upon the lower structure, wherein the first and the second capacitive plates are electrostatically coupled to each other.

39. The apparatus of claim 38, wherein the deflection sensor further comprises:
deflection sensor electronics coupled to the first and second capacitive plates and further coupled to the deflection mechanism to provide control of the variable gap.

* * * * *

UNITED STATES PATENT AND TRADEMARK OFFICE
CERTIFICATE OF CORRECTION

| | |
|---|---|
| PATENT NO. | : 7,025,324 B1 |
| APPLICATION NO. | : 10/336625 |
| DATED | : April 11, 2006 |
| INVENTOR(S) | : Slocum et al. |

It is certified that error appears in the above-identified patent and that said Letters Patent is hereby corrected as shown below:

Column 3, line 8 delete "BRIEF DESCIPTION OF TUE DRAWINGS" and replace with -- BRIEF DESCRIPTION OF THE DRAWINGS--.

Column 4 line 20 delete "flow channels 201a, 201" and replace with --flow channels 201a, 201b--.

Column 6, line 6 delete "or a closed." and replace with --or closed.--.

Column 6, line 11, delete "magnitude the force 130, 132" and replace with --magnitude of the force 130, 132--.

Column 6, line 12 delete "that inner portion 120" and replace with --of the inner portion 120--.

Column 6, line 42 delete "ten nanometer" and replace with --ten nanometers--.

Column 7, line 46 delete "that the when" and replace with --that when--.

Column 7, line 58 delete "can also includes" and replace with --can also include--.

Columns 7-8, lines 67-1 delete ", and indication" and replace with --, an indication--.

Column 8, line 64 delete "The uppers structure 620," and replace with --The upper structure 620,--.

Column 9, line 9 delete "silicon the lower" and replace with --silicon and the lower--.

Column 9, line 57 delete "bent by to a" and replace with --bent to a--.

UNITED STATES PATENT AND TRADEMARK OFFICE
CERTIFICATE OF CORRECTION

PATENT NO. : 7,025,324 B1
APPLICATION NO. : 10/336625
DATED : April 11, 2006
INVENTOR(S) : Slocum et al.

It is certified that error appears in the above-identified patent and that said Letters Patent is hereby corrected as shown below:

Column 10, line 33 delete "well-known" and replace with --well known--.

Signed and Sealed this

Twenty-first Day of November, 2006

JON W. DUDAS
*Director of the United States Patent and Trademark Office*